(12) United States Patent
Dayton et al.

(10) Patent No.: US 8,537,001 B1
(45) Date of Patent: *Sep. 17, 2013

(54) SYSTEM, METHOD, AND KIT FOR MONITORING AN ENVIRONMENT

(71) Applicant: American Messaging Services, LLC, Lewisville, TX (US)

(72) Inventors: Douglas C. Dayton, Harvard, MA (US); Sung Park, Newton, MA (US); Mark R. Florence, Newton, MA (US)

(73) Assignee: American Messaging Services, LLC, Lewisville, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/662,683

(22) Filed: Oct. 29, 2012

Related U.S. Application Data

(63) Continuation of application No. 12/043,250, filed on Mar. 6, 2008, now Pat. No. 8,299,917.

(60) Provisional application No. 60/905,530, filed on Mar. 6, 2007, provisional application No. 60/982,098, filed on Oct. 23, 2007.

(51) Int. Cl.
*G08B 1/08* (2006.01)

(52) U.S. Cl.
USPC .............. 340/539.14; 340/539.1; 340/539.12; 340/573.1

(58) Field of Classification Search
USPC ...................................................... 340/539.14
See application file for complete search history.

(56) References Cited

U.S. PATENT DOCUMENTS

| | | | |
|---|---|---|---|
| 5,917,414 A * | 6/1999 | Oppelt et al. ............... 340/573.1 |
| 6,956,497 B1 * | 10/2005 | Hindus et al. .................. 340/8.1 |
| 8,299,917 B2 * | 10/2012 | Dayton et al. ........... 340/539.14 |
| 2004/0061607 A1 * | 4/2004 | Pargman .................. 340/539.15 |
| 2005/0237207 A1 * | 10/2005 | Gilbert et al. .............. 340/573.1 |
| 2008/0238660 A1 * | 10/2008 | Dayton et al. ........... 340/539.14 |
| 2008/0238662 A1 * | 10/2008 | Dayton et al. ........... 340/539.22 |
| 2008/0238692 A1 * | 10/2008 | Dayton et al. ............. 340/573.1 |
| 2008/0294462 A1 * | 11/2008 | Nuhaan et al. ..................... 705/3 |

* cited by examiner

*Primary Examiner* — Travis Hunnings
(74) *Attorney, Agent, or Firm* — Ulmer & Berne LLP (57) ABSTRACT

In embodiments of the present invention, systems and methods for remotely monitoring an environment may include receiving sensor data from a sensor placed in an environment. The sensor data may be processed to obtain monitoring information for the environment. The monitoring information may be transmitted over a network.

20 Claims, 4 Drawing Sheets

SYSTEM, METHOD, AND KIT FOR MONITORING AN ENVIRONMENT

CROSS-REFERENCE TO RELATED APPLICATIONS

This application is a continuation of U.S. patent application Ser. No. 12/043,250, entitled "System, Method, and Kit for Monitoring an Individual Remotely," filed Mar. 6, 2008, which claims the benefit of the following provisional applications: U.S. Provisional Application No. 60/905,530, filed Mar. 6, 2007; and U.S. Provisional Application No. 60/982,098, filed Oct. 23, 2007, each of which is hereby incorporated by reference in its entirety.

BACKGROUND

1. Field

The methods and systems described herein relate to motion-sensitive, networked devices.

2. Description of the Related Art

Individuals living by themselves, especially senior citizens, are at risk of being injured without a way to contact help. Motion-triggered and networked devices may detect an absence of activity and notify a remote location.

SUMMARY

Provided herein are methods and systems for monitoring an individual at a remote location. A method and system of monitoring an individual at a remote location may comprise providing at least one of a monitoring device in the form factor of a household decoration, such as a picture frame. The method and system of monitoring may further comprise at least one of a receiving device in the form factor of a household decoration, such as a picture frame. The method and system of monitoring a remote individual may also comprise a wireless network, such as a one-way paging network for communicating between the monitoring and receiving devices. The form factor for the monitoring devices and the receiving devices may comprise any household object, including, but not limited to a lamp, a picture frame, a mat, a home appliance, or any other household object.

In an aspect of the invention, a system and method of monitoring an individual at a location may comprise providing a sensor integrated in a monitoring object at a first location, the monitoring object configured as a household item, associating the sensor with an environment of an individual at the first location, associating the sensor with a network, providing monitoring information at a second location, and transmitting the monitoring information from the first location to the second location over the network. In the system and method, the sensor may be a plurality of sensors. In the system and method, the sensor may be at least one of a motion-sensor, an infrared motion sensor, a temperature sensor, a thermostat, an audio sensor, a vibration sensor, and some other sensor. In the system and method, the object may be at least one of a picture frame, a floor mat, a lamp, a household appliance, and some other object. In the system and method, the first location may be a home. In the system and method, the first location may be an apartment. In the system and method, the first location may be a medical facility. In the system and method, the network may be an intranet. In the system and method, the network may be an internet. In the system and method, the network may be a telecommunications network. In the system and method, the monitoring information may comprise information regarding the cessation of movement. In the system and method, transmitting may comprise one-way paging.

In an aspect of the invention, a system of monitoring an individual at a location may comprise a sensor integrated in a first object for monitoring an individual at a first location, a transmitter associated with the sensor for transmitting a monitoring information, a receiver integrated in a second object for receiving the monitoring information at a second location, an indicator associated with the receiver for indicating a status in response to the monitoring information, and a network for transmitting the monitoring information from the transmitter to the receiver. In the system, the sensor may be a plurality of sensors. In the system, the sensor may be at least one of a motion-sensor, an infrared motion sensor, a temperature sensor, a thermostat, an audio sensor, a vibration sensor, and some other sensor. In the system, the first object may be at least one of a picture frame, a floor mat, a lamp, a household appliance, and some other object. In the system, the second object may be at least one of a picture frame, a household appliance, and some other object. In the system, the first location may be at least one of a home, an apartment, a medical facility, and some other location. In the system, the second location may be at least one of a home, an apartment, a medical facility, and some other location. In the system, the network may be an intranet. In the system, the network may be an internet. In the system, the network may be a telecommunications network. In the system, the monitoring information may comprise information regarding the cessation of movement. In the system, transmitting may comprise one-way paging.

In an aspect of the invention, a system and method of remotely monitoring an individual may include providing a sensor integrated in a monitoring object at a first location, the monitoring object configured as a household item, associating the sensor with the environment of an individual at the first location, associating the sensor with a network, processing sensor data to obtain monitoring information for the activity of the individual in the environment, and transmitting the monitoring information over the network from the first location to a receiving object at a second location. In the system and method, the sensor may be one of a plurality of sensors. In the system and method, the sensor may be at least one of a motion-sensor, an infrared motion sensor, a temperature sensor, a thermostat, an audio sensor, and a vibration sensor. In the system and method, the object may be at least one of a picture frame, a floor mat, a lamp, and a household appliance. In the system and method, the network may be a telecommunications network. In the system and method, the network may be a wireless network. In the system and method, transmitting may include one-way paging. In the system and method, the monitoring information may include information regarding the cessation of activity. In the system and method, processing may include determining if sensor inputs were obtained within a predetermined time interval. In the system and method, processing may include comparing sensor inputs against a map relating timing of events with either a clock or a calendar expectation. The system and method may further include programming the monitoring object with a standard map of activities to facilitate processing. The system and method may further include calibrating the monitoring object with a sample of ambient signals in the monitored individual's environment to establish a comparison map to facilitate processing. The system and method may further include setting an amount of time within which the sensor must sense an activity. In the system and method, the receiving object may be adapted to display a signal based on the transmitted monitoring information. In the system and method, the receiving object may be adapted to emit a signal based on the transmitted monitoring information. In the system and method, the receiving object may be configured as a household object.

In an aspect of the invention, a kit for remotely monitoring an individual may include a household object for placement in the environment of an individual to be monitored which may include an integrated sensor for collecting activity data for an individual, internal logic for processing the activity information according to a map of expected activity to obtain monitoring information and a transmission facility for transmitting the monitoring information over a pager network, a receiving object for receiving the monitoring information which may include an antenna for receiving the transmitted monitoring information and a display for displaying the status of the individual as indicated by the monitoring information, and a service for enabling the transmission of the monitoring information from the household monitoring object to the receiving object. In the kit, the sensor may be a plurality of sensors. In the kit, the sensor may be at least one of a motion-sensor, an infrared motion sensor, a temperature sensor, a thermostat, an audio sensor, and a vibration sensor. In the kit, the household object may be at least one of a picture frame, a floor mat, a lamp, and a household appliance. In the kit, transmitting may include one-way paging. In the kit, the monitoring information may include information regarding the cessation of activity. In the kit, processing may include determining if sensor inputs were obtained within a predetermined time interval. In the kit, processing may include comparing sensor inputs against a map relating timing of events with either a clock or a calendar expectation. The kit may further include a programming interface of the household monitoring object to program the monitoring object with a standard map of activities to facilitate processing. The kit may further include a calibration interface of the household monitoring object to obtain a sample of ambient signals in the monitored individual's environment for establishing a comparison map to facilitate processing. The kit may further include a switch associated with the sensor for setting an amount of time within which the sensor must sense an activity. In the kit, the receiving object may be adapted to display a signal based on the transmitted monitoring information. In the kit, the receiving object may be adapted to emit a signal based on the transmitted monitoring information. In the kit, the monitoring object and receiving object may automatically establish a connection once powered.

In an aspect of the invention, a system and method of remotely monitoring an individual may include providing a sensor integrated in a monitoring object at a first location, the monitoring object configured as a household item, associating the sensor with an environment of an individual at the first location, associating the sensor with a network, processing sensor data to obtain monitoring information for the activity of the individual in the environment, and transmitting the monitoring information over the network from the first location to a receiving object at a second location, the receiving object configured as a household item. In the system and method, the sensor may be one of a plurality of sensors. In the system and method, the sensor may be at least one of a motion-sensor, an infrared motion sensor, a temperature sensor, a thermostat, an audio sensor, and a vibration sensor. In the system and method, the receiving object may be a picture frame. The picture frame may hold a picture of the individual being monitored. In the system and method, the monitoring object may be a picture frame. In the system and method, the network may be a telecommunications network. In the system and method, the network may be a wireless network. In the system and method, transmitting may include one-way paging. In the system and method, the monitoring information may include information regarding the cessation of activity. In the system and method, processing may include determining if sensor inputs were obtained within a predetermined time interval. In the system and method, processing may include comparing sensor inputs against a map relating timing of events with either a clock or a calendar expectation. The system and method may further include programming the monitoring object with a standard map of activities to facilitate processing. The system and method may further include calibrating the monitoring object with a sample of ambient signals in the monitored individual's environment to establish a comparison map to facilitate processing. The system and method may further include setting an amount of time within which the sensor must sense an activity. In the system and method, the receiving object may be adapted to display a signal based on the transmitted monitoring information. In the system and method, the receiving object may be adapted to emit a signal based on the transmitted monitoring information.

In an aspect of the invention, a system and method of remotely monitoring a plurality of individuals may include providing a plurality of monitoring objects, wherein each monitoring object is associated with the environment of one of the plurality of individuals, integrating a sensor into each monitoring object, wherein the sensor collects activity data for the individual associated with the monitoring object, processing sensor data at each monitoring object to obtain monitoring information for the activity of the individual associated with the monitoring object, and transmitting the monitoring information obtained with each monitoring object over a network to a receiving object, wherein the receiving object displays a picture associated with the particular individual being monitored at the time that it displays information about that individual. In the system and method, the sensor may be one of a plurality of sensors. In the system and method, the sensor may be at least one of a motion-sensor, an infrared motion sensor, a temperature sensor, a thermostat, an audio sensor, and a vibration sensor. In the system and method, the monitoring object may be configured as a household item. In the system and method, the network may be a telecommunications network. In the system and method, the network may be a wireless network. In the system and method, transmitting may include one-way paging. In the system and method, the monitoring information may include information regarding the cessation of activity. In the system and method, processing may include determining if sensor inputs were obtained within a predetermined time interval. In the system and method, processing may include comparing sensor inputs against a map relating timing of events with either a clock or a calendar expectation. The system and method may further include programming the monitoring object with a standard map of activities to facilitate processing. The system and method may further include calibrating the monitoring object with a sample of ambient signals in the monitored individual's environment to establish a comparison map to facilitate processing. The system and method may further include setting an amount of time within which the sensor must sense an activity. In the method and system, the receiving object may be adapted to display a signal based on the transmitted monitoring information. In the method and system, the receiving object may be adapted to emit a signal based on the transmitted monitoring information.

In an aspect of the invention, a system and method of remotely monitoring an individual may include providing a sensor integrated in a monitoring object at a first location, the monitoring object configured as a picture frame, associating the sensor with an environment of an individual at the first location, associating the sensor with a network, processing sensor data to obtain monitoring information for the activity of the individual in the environment, and transmitting the monitoring information over the network from the first location to a receiving object at a second location, the receiving object configured as a picture frame. In the system and method, the sensor may be one of a plurality of sensors. In the system and method, the sensor may be at least one of a motion-sensor, an infrared motion sensor, a temperature sensor, a thermostat, an audio sensor, and a vibration sensor. In the system and method, the picture frame may hold a picture of the individual being monitored. In the system and method, the picture frame may hold a picture of the monitoring party. In the system and method, the network may be a telecommunications network. In the system and method, the network may be a wireless network. In the system and method, transmitting may include one-way paging. In the system and method, the monitoring information may include information regarding the cessation of activity. In the system and method, processing may include determining if sensor inputs were obtained within a predetermined time interval. In the system and method, processing may include comparing sensor inputs against a map relating timing of events with either a clock or a calendar expectation. The system and method may further include programming the monitoring object with a standard map of activities to facilitate processing. The system and method may further include calibrating the monitoring object with a sample of ambient signals in the monitored individual's environment to establish a comparison map to facilitate processing. The system and method may further include setting an amount of time within which the sensor must sense an activity. In the system and method, the receiving object may be adapted to display a signal based on the transmitted monitoring information. In the system and method, the receiving object may be adapted to emit a signal based on the transmitted monitoring information.

In an aspect of the invention, a kit for remotely monitoring an individual may include a picture frame for placement in the environment of an individual to be monitored which may include an integrated sensor for collecting activity data for an individual, internal logic for processing the activity information according to a map of expected activity to obtain monitoring information and a transmission facility for transmitting the monitoring information over a pager network, a receiving object for receiving the monitoring information which may include an antenna for receiving the transmitted monitoring information and a display for displaying the status of the individual as indicated by the monitoring information, and a service for enabling the transmission of the monitoring information from the household monitoring object to the receiving object. In the kit, the sensor may be a plurality of sensors. In the kit, the sensor may be at least one of a motion-sensor, an infrared motion sensor, a temperature sensor, a thermostat, an audio sensor, and a vibration sensor. In the kit, the receiving object may be at least one of a picture frame, a floor mat, a lamp, and a household appliance. In the kit, transmitting may include one-way paging. In the kit, the monitoring information may include information regarding the cessation of activity. In the kit, processing may include determining if sensor inputs were obtained within a predetermined time interval. In the kit, processing may include comparing sensor inputs against a map relating timing of events with either a clock or a calendar expectation. The kit may further include a programming interface of the household monitoring object to program the monitoring object with a standard map of activities to facilitate processing. The kit may further include a calibration interface of the household monitoring object to obtain a sample of ambient signals in the monitored individual's environment for establishing a comparison map to facilitate processing. The kit may further include a switch associated with the sensor for setting an amount of time within which the sensor must sense an activity. In the kit, the receiving object may be adapted to display a signal based on the transmitted monitoring information. In the kit, the receiving object may be adapted to emit a signal based on the transmitted monitoring information. In the kit, the picture frame and receiving object may automatically establish a connection once powered.

These and other systems, methods, objects, features, and advantages of the present invention will be apparent to those skilled in the art from the following detailed description of the preferred embodiment and the drawings. All documents mentioned herein are hereby incorporated in their entirety by reference.

BRIEF DESCRIPTION OF THE FIGURES

The invention and the following detailed description of certain embodiments thereof may be understood by reference to the following figures.

DETAILED DESCRIPTION

A wireless home monitoring system for monitoring the activity of an individual may comprise a monitoring device, a network and a receiving device. The monitoring device may comprise a sensor in a form factor where the form factor may be a common household decoration, such as a picture frame. The receiving device may comprise a visual and/or audio status indicator in a form factor where the form factor may also be a common household decoration, such as a picture frame. The network may comprise a one-way paging network, a two-way paging network, a cellular network, a wireless network, the Internet, and the like. The wireless household monitoring system may be simple to install out of the box and may enable the communication of two or more households at a relatively passive level. This system may provide a non-intrusive and relatively passive reassurance to remote family members, or other individuals who are monitoring, that the individual being monitored, for example, a senior member of their family living alone, is carrying on life as normal. Should there be an interruption of the individual's normal routine within their home, this system may notify the other connected family members or monitoring individuals of that change. This invention may utilize network technology, such as one-way pager technology, to link the remote elements of the system and simple sensors and I/O to detect and communicate.

Figure 1:
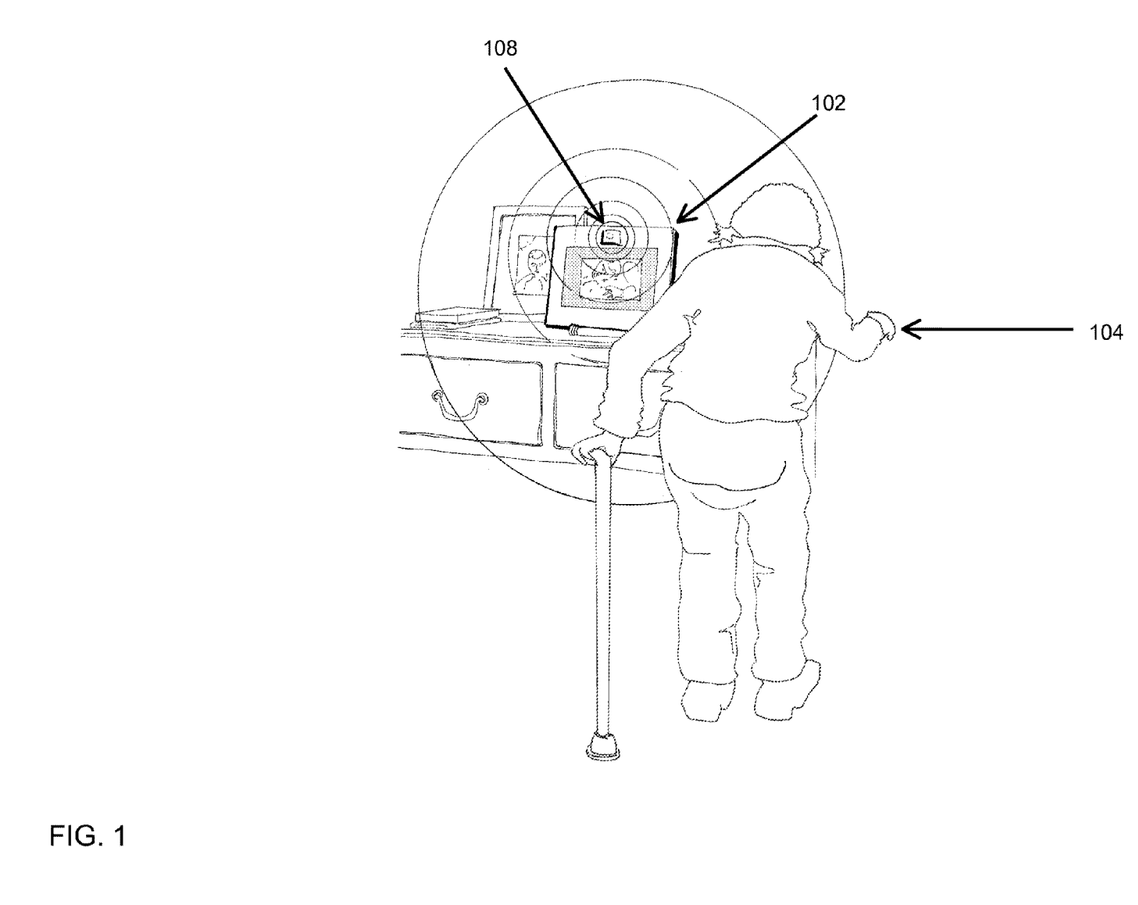
FIG. 1 depicts a sensing device of the household monitoring system in sensing mode.

Referring to FIG. 1, a network of monitoring devices may enable monitoring of an individual's movements and status from a remote location. In use, the monitored individual 104 may have the monitoring device 102 with associated sensor 108 present in their area of activity. When the presence or activity of monitored individual activates the sensor 108, the monitoring device 102 may accumulate data regarding the monitored individual.

In one embodiment, the physical form of the monitoring component 102 of the system may be configured to be a picture frame that may hold a picture of the family members or friends that are connected by this service. In other embodiments, the form factor may be some other non-obtrusive household item. For example, in one embodiment, the form factor of a monitoring device may be a mat. In another embodiment, the form factor of a monitoring device may be a faucet. In a further embodiment, the form factor of a monitoring device may be a lamp.

In an embodiment, the form factor may comprise electronics that monitor the activities of an individual 104 at a first location. In some embodiments, the form factor monitoring comprises using sensors 108, such as motion sensors, infrared sensors, audio pickups or vibration sensors, and the like in association with the monitoring device 102. In some further embodiments, the monitoring may include using other sensors that can detect a signature of normal personal activities around the location.

In an embodiment, the monitoring device 102 may comprise an antenna for sending communications to a receiving device. The antenna may be an internal antenna or an external antenna.

Figure 2:
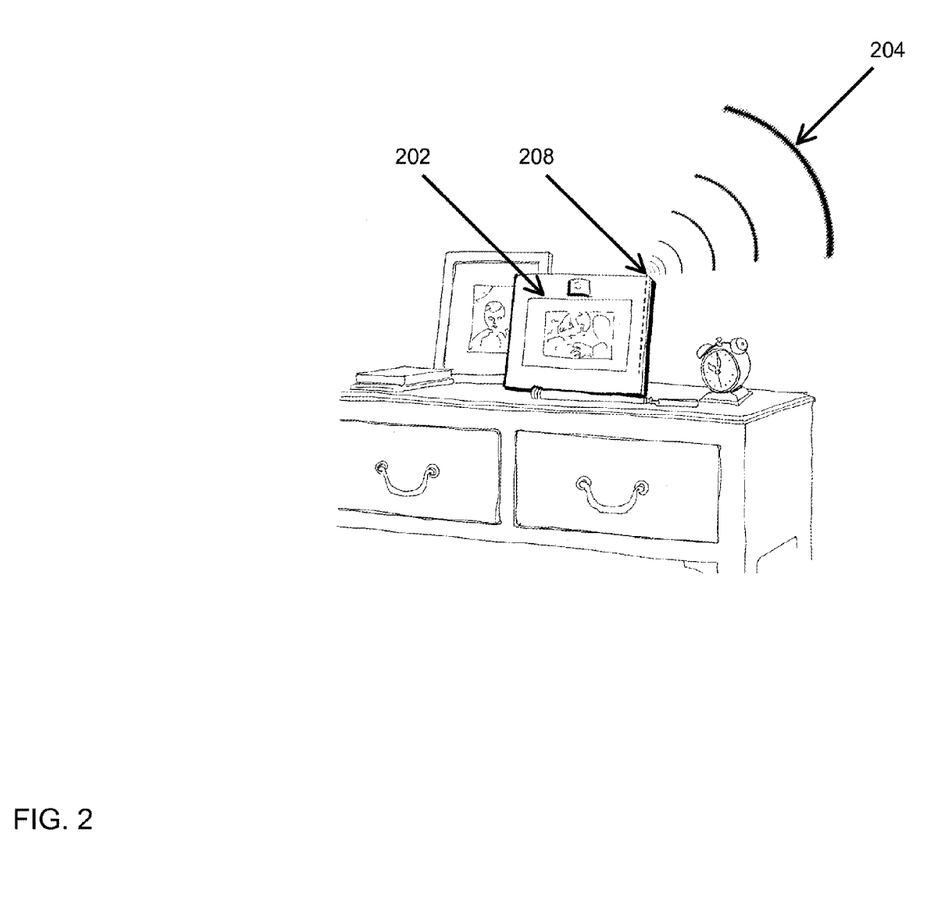
FIG. 2 depicts a transmitting device of the household monitoring system in transmitting mode.

Referring to FIG. 2, the monitoring component may enable monitoring by processing detected activity signatures. In one embodiment, the monitoring component 202 may compare the detected activity signatures against a time measure provided by a real-time clock that may be incorporated in the electronics. In another embodiment, the monitoring component may compare the activity signature against a map of standard activities. In some embodiments, the map of standard activities may be recorded in the device's programming mode. For example, in order to calibrate the device 102 to prepare the map of standard activities, the device 102 may be used to record the monitored individual's 104 daily activities using the sensors 108 in the device 102 to collect the information, such as a level of activity or inactivity, a time of day when active, and the like. In other embodiments, the map of standard activities may be compiled and loaded into the device at the time of installation. In certain embodiments, every time the sensors 108 detect activity or inactivity, a signal may be sent to a receiving device to alert a monitor of the activity or inactivity.

In an embodiment, the device's internal logic may determine if the detected activity signature is within or outside of a control range. In some embodiments, if the device detects a deviation, the device may transmit a signal 204 to a receiving device. For example, a map of standard activities may indicate that the monitored individual should be detected at least once during a pre-determined time interval, and if there is no detection during the interval, a signal may be sent to a receiving device. In one embodiment, the device may transmit a signal 204 via pager electronics. In some embodiments, using the pager electronics may include using an internal, integrated but concealed antenna 208 to communicate to the local pager network. In some other embodiments, using the pager electronics may include using an external antenna.

In an embodiment, the monitoring component may enable monitoring by simply transmitting each detection event. For example, each time the monitored individual is detected, the device 102 may send a signal to the receiving device.

Figure 3:
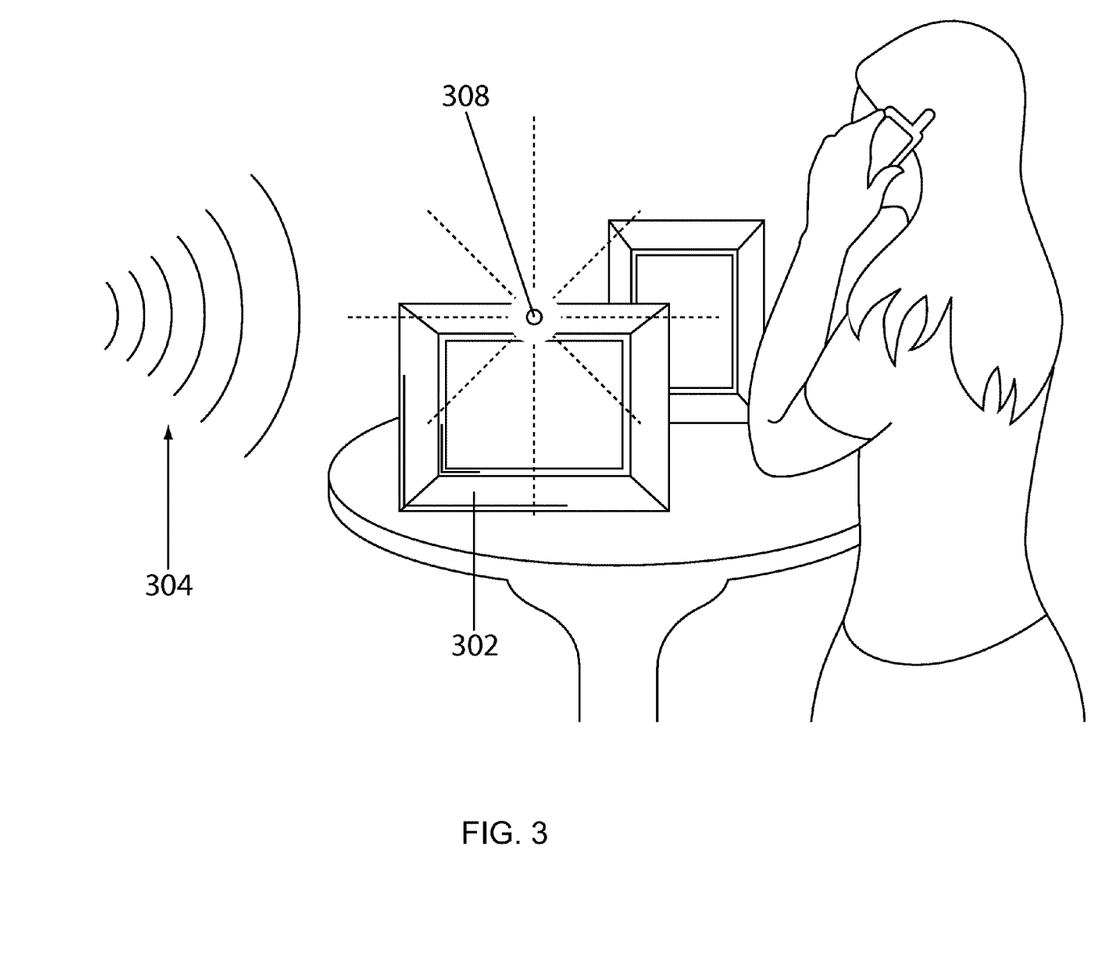
FIG. 3 depicts a receiving device of the household monitoring system in alert mode.

Referring now to FIG. 3, the receiving component of the system located at the monitoring location may be configured to look like a household decoration.

In one embodiment, the receiving component may be configured as a picture frame 302. In some embodiments the picture frame 302 may hold a picture of the individual monitored by this service. In other embodiments, the receiving component may utilize a different form factor such as some other familiar, decorative, useful or non-obtrusive household item.

In an embodiment, the receiver may comprise electronics that may receive a targeted communication 304 from a monitoring device 102. In some embodiments, the targeted communication 304 may be transmitted by a pager network, the Internet, a Bluetooth or other wireless connection, a cellular network, and the like. In other embodiments, the receiver may analyze the targeted communication and create an output in response to the targeted communication. For example, in the absence of a signal from the monitoring device 102 of a deviant activity or inactivity, the receiver may have an output to signify a normal "all-is-well" mode. For example, in response to the "all-is-well" mode, the receiver may display a discrete green light 308 that may easily be perceived by a monitoring individual. In another example, the output may be the absence of a light. In other embodiments, in response to a deviation in the activity signature, the monitoring component 102 may signal to the receiving component a change in the output of the light display. For example, the light display may change to yellow or red or may increase in intensity. The change may depend upon the type and magnitude of the deviation. In other embodiments, the receiver may include a speaker, which may be small and/or invisible, and which may emit an audio signal if a deviation is detected. In some other embodiments, the speaker may emit an audio signal if the distress signal received is urgent. In other embodiments, the receiver may enable an individual monitoring the receiver to respond to the change of status indication such as by calling the monitored individual or by calling another individual or agency to investigate the signal.

Figure 4:
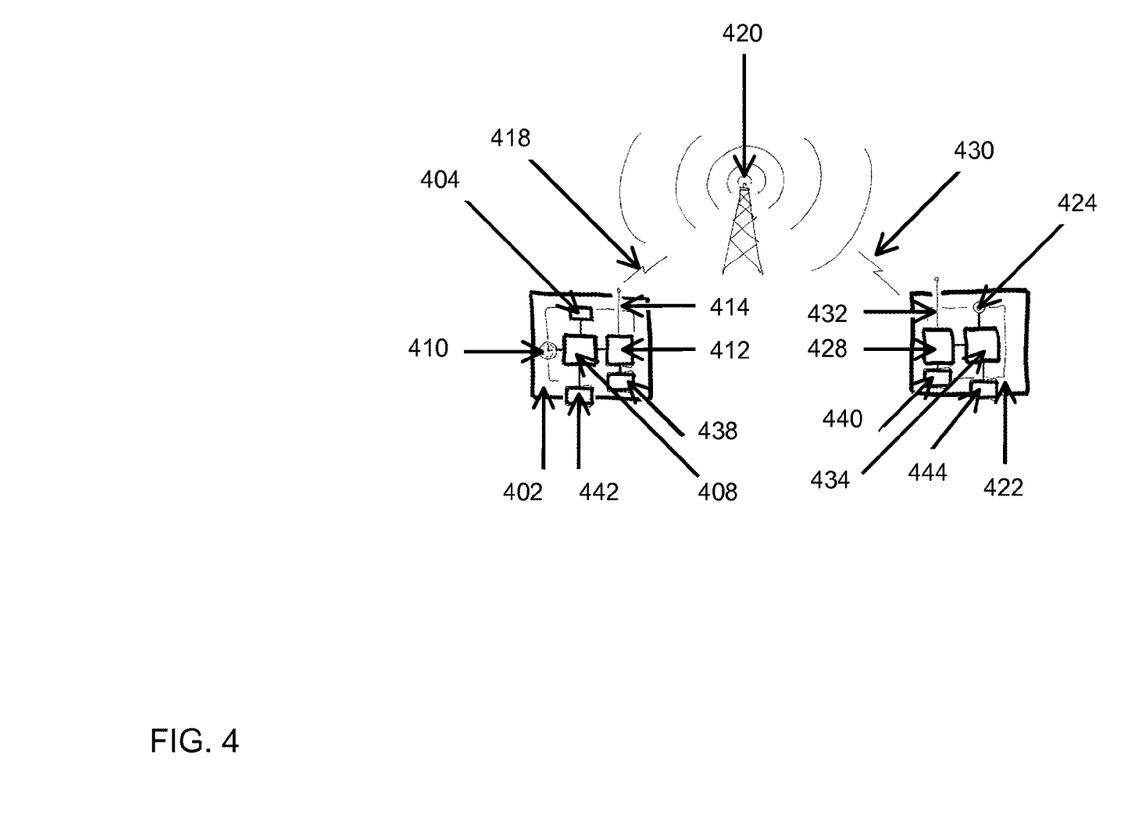
FIG. 4 depicts a remote monitoring communication system.

Now referring to FIG. 4, the household monitoring system may comprise 1) the monitor; 2) the receiver, and 3) a service arrangement for the communication transmission network linking the monitor and the receiver. In some embodiments, there may be a plurality of monitors. In other embodiments, there may be a plurality of receivers.

In one embodiment, the monitor may be configured to be a picture frame 402, such as a frame that can hold a picture of the individual or individuals that are connected by the service. In another embodiment, a detector 404 may detect the signature of normal personal activities around the home of a monitored individual. The detector 404 may be a motion detector, an infrared detector, and the like. In other embodiments, the detector 404 may be another activity detector such as an audio pickup, a vibration sensor, or other suitable sensor. In some embodiments, a logic element with internal memory 408 may integrate a sensor input and measure the input against an internal clock/calendar 410 to determine if the situation is normal or anomalous. In some other embodiments, the measure of normalcy may be as simple as a determination that sensor/detector inputs were obtained within a predetermined time interval or may be as complex as a comparison of incoming inputs against a more complex map relating timing of events with either a clock or a calendar expectation. Programming the monitoring device 102 may be enabled by toggles or switches on the device itself that indicate time intervals for monitoring. In other embodiments, the device 102 may have an input connector in order to receive programming. In other embodiments, in response to a determination that the inputs represent a deviation from normal by the logic element, the logic element may power a communications system, such as a wireless pager module 412, and direct the communications system to send a signal on a network to the location or locations, such as a pager address or a plurality of pager addresses, that have been pre-loaded into the logic unit's memory. In some embodiments, an embedded antenna 414 may transmit the pager signal 418 to the local tower 420 and via the network to the receiving unit.

In another aspect of the invention, the receiving unit 422 may be, similar to the monitoring unit, configured to be a picture frame that can hold a picture of the family members or friends that are connected by this service. In other embodiments, the form factor may be some other familiar, decorative, useful and non-obtrusive household item. In some embodiments, the receiving unit may be a remote annunciator for the monitor. In some other embodiments, the receiving unit may display an illuminated indicator 424 of the status at the monitored location. The light color may indicate the status of the monitored individual. In some embodiments the light colored green may indicate a normal status. In other embodiments, the light colored yellow may indicate caution, such as for example, if the last time interval or control point is missing. In further embodiments, the light colored red may indicates a warning, such as there is a severe deviation from the normal status. In some embodiments, the light indicator may be supplemented by an audio feedback device. In other embodiments, the light indicator may be supplemented by other means of feedback. In further embodiments, in response to receiving an incoming signal 430 with the embedded antenna 432, an always-on pager network receiver 428 may pass the incoming information to the logic unit 434 that may change the status display and may initiate other warning output.

In one embodiment, the monitor and receiver units may be wireless, cordless devices powered by an electrical power cord or onboard batteries 438, 440 that supply the power needs of all electronic elements including the logic, memory, clock and pager components. In an embodiment, the batteries may be replaceable and/or rechargeable. In some embodiments, both modules can be corded to plug into household power. In further embodiments, a user control may be provided on both the monitor and the receiver. In some other embodiments, the monitor and the receiver may have a toggling power switch. In other embodiments, the monitor may have an external panel 442 comprising the power switch and a connector for recharging. In one embodiment, the monitor may have a switch that is set to the amount of time within which the motion detector must sense motion or the monitor will send a warning signal to the receiver. In another embodiment, the monitor may have a "Learn" mode to record a sample of ambient signals in the environment to establish a NORMAL comparison map for more sophisticated monitoring. In other embodiments, there may be an input connector from which a predetermined comparison table may be loaded. In some other embodiments, the receiver may have an external panel 444 comprising the power switch and a connector for recharging. In some embodiments, both the monitor and the receiver may comprise modules that have a battery door to change the battery.

In an embodiment, the components of the system may be obtained together as an out-of-the-box kit. For example, the kit may include a household object, such as a picture frame, for placement in the vicinity of an individual to be monitored. The picture frame may include an integrated sensor for collecting activity data for an individual, internal logic for processing the activity information according to a map of expected activity to obtain monitoring information and a transmission facility for transmitting the monitoring information over a network. Also included in the kit may be a receiving object for receiving the monitoring information. The receiving object may include an antenna for receiving the transmitted monitoring information and a display for displaying the status of the individual as indicated by the monitoring information, such as light. The kit may also comprise a service for enabling the transmission of the monitoring information from the household monitoring object to the receiving object. The service may be provided by a wireless provider, pager network operator, Internet provider, and the like. The components of the kit may come pre-matched so that the monitoring object and receiving object may be able to establish a connection automatically once powered.

What is claimed is:

1. A monitoring system, comprising:
a first object comprising a sensor, the first object for placement in a first environment to collect activity data from the first environment, the first object comprising:
a processor for processing sensor data from the sensor, the processor configured to:
establish a map of standard activities of the individual through recording a sample of at least one activity in the first environment,
generate monitoring information for the first environment based on the map of standard activities for the first environment; and
a transmitter associated with the processor for transmitting the monitoring information over a network; and
a second object comprising a receiver for receiving the transmitted monitoring information, the second object for placement in a second environment.

2. The system of claim 1, wherein the first object is operable in each of a plurality of operational modes.

3. The system of claim 2, wherein one of the plurality of operational modes is a programming mode for programming the first object with the map of standard activities.

4. The system of claim 2, wherein one of the plurality of operational modes is a calibration mode for collecting a sample of ambient signals in the first environment to establish the map of standard activities.

5. The system of claim 1, wherein at least one of the first object and the second object is configured as a household object.

6. The system of claim 5, wherein the household object is any of a lamp, a picture frame, a mat, and a home appliance.

7. The system of claim 1, wherein the sensor is any of a motion-sensor, an infrared motion sensor, a temperature sensor, a thermostat, an audio sensor, and a vibration sensor.

8. The system of claim 1, wherein the sensor is a plurality of sensors.

9. The system of claim 1, wherein the network comprises a telecommunications network.

10. The system of claim 1, wherein the network comprises a wireless network.

11. The system of claim 1, wherein the second object comprises a status indicator configured to display an indication of activity based on the monitoring information.

12. A method of monitoring activity in an environment, comprising:
placing a sensor in a first environment, the sensor coupled to a first object and configured to generate sensor data;
establishing a map of standard activities in the first environment, wherein a sample of at least one activity in the environment is recorded to establish the map of standard activities;

processing the sensor data using the map of standard activities to obtain monitoring information for the activity in the environment; and transmitting the monitoring information over a network to a second object in a second environment; and displaying at the second object an indication of activity in the first environment based on the monitoring activity.

13. The method of claim 12, wherein the sensor is one of a plurality of sensors.

14. The method of claim 12, wherein the sensor is any of a motion-sensor, an infrared motion sensor, a temperature sensor, a thermostat, an audio sensor, and a vibration sensor.

15. The method of claim 12, wherein at least one of the first object and the second object is configured as a household object.

16. The method of claim 12, wherein transmitting the monitoring information over a network comprises transmitting the monitoring information over a telecommunications network.

17. The method of claim 12, wherein transmitting the monitoring information over a network comprises transmitting the monitoring information over wireless network.

18. A method of monitoring activity in an environment, comprising:

receiving first sensor data from a sensor placed in an environment;

based on the first sensor data, establishing a map of standard activities in an environment, wherein a sample of at least one activity in the environment is recorded to establish the map of standard activities;

receiving second sensor data from the sensor placed in the environment;

processing the second sensor data using the map of standard activities to obtain monitoring information for the environment; and transmitting the monitoring information over a network.

19. The method of claim 18, wherein the first sensor data is received during a programming mode of operation.

20. The method of claim 18, wherein the sensor is any of a motion-sensor, an infrared motion sensor, a temperature sensor, a thermostat, an audio sensor, and a vibration sensor.

* * * * *